(12) United States Patent
Chen

(10) Patent No.: US 9,429,517 B2
(45) Date of Patent: Aug. 30, 2016

(54) LIGHTING DEVICE WITH EXPANDED DETECTION RANGE

(71) Applicant: Kaipo Chen, Taoyuan (TW)

(72) Inventor: Kaipo Chen, Taoyuan (TW)

( * ) Notice: Subject to any disclaimer, the term of this patent is extended or adjusted under 35 U.S.C. 154(b) by 63 days.

(21) Appl. No.: 14/621,400

(22) Filed: Feb. 13, 2015

(65) Prior Publication Data

US 2015/0160130 A1    Jun. 11, 2015

Related U.S. Application Data

(63) Continuation-in-part of application No. 13/220,720, filed on Aug. 30, 2011, now Pat. No. 9,228,731.

(30) Foreign Application Priority Data

Jan. 14, 2015   (CN) .......................... 2015 1 0018134

(51) Int. Cl.
| | | |
|---|---|---|
| G01N 21/55 | (2014.01) |
| H04N 7/18 | (2006.01) |
| F21V 23/04 | (2006.01) |
| H05B 37/02 | (2006.01) |
| H05B 33/08 | (2006.01) |
| F21K 99/00 | (2016.01) |
| F21S 8/04 | (2006.01) |
| F21W 111/00 | (2006.01) |
| F21Y 101/02 | (2006.01) |
| F21Y 103/02 | (2006.01) |

(52) U.S. Cl.
CPC ................. *G01N 21/55* (2013.01); *F21K 9/13* (2013.01); *F21S 8/04* (2013.01); *F21V 23/0442* (2013.01); *H04N 7/183* (2013.01); *H05B 33/0803* (2013.01); *H05B 37/0227* (2013.01); *F21W 2111/00* (2013.01); *F21Y 2101/02* (2013.01); *F21Y 2103/022* (2013.01); *G01N 2201/061* (2013.01); *G01N 2201/068* (2013.01)

(58) Field of Classification Search
CPC ..................... F21Y 2101/02; F21Y 2103/022; G01N 21/55; G01N 2101/061; G01N 2201/068; F21K 9/13; F21V 23/0442; H04N 7/183; H05B 33/0803; H05B 37/0227; F21W 2111/00
USPC ...................................... 362/311.02
See application file for complete search history.

(56) References Cited

U.S. PATENT DOCUMENTS

2014/0009936 A1 * 1/2014 Hata ....................... F21K 9/135
                                                          362/235

(Continued)

FOREIGN PATENT DOCUMENTS

| EP | 2 273 190 | * | 1/2011 |
| WO | WO 2013/153738 | * | 10/2013 |

*Primary Examiner* — Laura Tso
(74) *Attorney, Agent, or Firm* — Leong C. Lei

(57) ABSTRACT

A lighting device with expanded detection range includes a housing, which receives a seat to which a detector is mounted and has a circumference along which LEDs are mounted to mount therein, a lens being fit to an opening formed in a top of the housing corresponding to the seat so that a distal end of the lens is exposed outside the housing; a light shielding hood having a top end extending to the housing and connected to the lens and a bottom fixed to the seat to block entry of external lighting; and a reflector assembly including a reflector that condenses a signal source arranged on a top thereof and having inside and outside reflection surfaces and further including a fixing sleeve fixed to a bottom thereof to couple with the detector.

4 Claims, 14 Drawing Sheets

(56) References Cited

U.S. PATENT DOCUMENTS

2014/0098548 A1* 4/2014 Huang ................ F21K 9/13
362/362

2014/0133154 A1* 5/2014 Ju ...................... F21V 29/89
362/294

2014/0140067 A1* 5/2014 Chen ................. F21K 9/135
362/294

* cited by examiner

LIGHTING DEVICE WITH EXPANDED DETECTION RANGE

CROSS-REFERENCE TO RELATED APPLICATION

This is a continuation-in-part of co-pending U.S. patent application Ser. No. 13/220,720 filed on Aug. 30, 2011 and owned by the present applicant.

TECHNICAL FIELD OF THE INVENTION

The present invention relates generally to a lighting device with an expanded detection range, which generally comprises a housing in which a reflector assembly and a lens are mounted so that a signal source, when guided in, is subjected to reflection to the detector so as to achieve expansion of the detection range and a light shielding hood that has a top end connected to the lens so that the detector is blocked by the light shielding hood from external lighting and thus the normal operation of detection can be maintained so as to be applicable to lighting fixtures including a detector.

DESCRIPTION OF THE PRIOR ART

Detectors and sensors generally have a fixed detection direction and a limited range of detection, for whatever types and quality they may be. It often needs to set up the location and orientation of a detector before use or an automatic adjustment structure must be included so that the function of detection can be properly performed when a target enters an effective detection range thereof. Examples are illustrated in U.S. Pat. Nos. 5,452,135, 5,227,632, 5,308,985, and 6,653,635, of which the contents are all related to applications for expanding the detection range of a detector with the detector being installed in associated with the direction for detection. However, no proposal has been made in improving the detection range of a combination of a lighting device and a detector.

A conventional lighting device is often provided with an adjustment structure that is composed of a rotary axle and a linkage to achieve the adjustment of the detection angle and direction. However, the adjustment that can be achieved is not good. The present inventor has proposed an improved lighting device, such as that disclosed in U.S. Pat. No. 7,327,254, in which a light-emitting diode (LED) based device is combined with a detector, but no conventional adjustment structure is included and instead, a light condensation cap is arranged outside the detector and extends beyond and is exposed outside a light cover so that the sensitivity of detection of the detector is not affected by light emitting from the LED inside the lighting device. However, the detection range that can be achieved with the detector is still insufficient (for the maximum range of detection is around 90 degrees in a practical application).

The present inventor subsequently proposed further improvements, such as U.S. Pat. No. 8,123,379, in which a spherical socket is provided to receive and hold a detector therein and a manual operation is available for adjusting a detection range of the detector (for example adjusting the direction of detection in a practical application). Although the detection range can be improved, there is insufficiency for practical uses.

The conventional lighting devices that are activated by a detector have the following disadvantages. (1) The arrangement space of the detector and the interior structure of the lighting device imposes limitations to the detection range, making it hard to expand and even though the direction of the detection range is adjusted, the range and distance of detection are still constrained. (2) The detector may erroneously operate due to reflection of the light from the LED by the light cover to incorrectly activate and de-activate.

In brief, from the above-discussed drawbacks, it is clear that the detection range is subjected to undesired constraint and is also readily affected by external lighting source so that the detection function of the lighting device cannot work properly and effectively. Further improvements are desired.

SUMMARY OF THE INVENTION

The present invention provides a reflector assembly that can be fit to and coupled with a detector. The reflector assembly comprises a reflector that guides a signal source arranged at a top thereof and the reflector assembly has a bottom that is fit to the detector. The detector is arranged on a seat located inside a housing. The housing has a top in which an opening is formed to receive a lens to fit therein. With two ends of a light shielding hood respectively fit to and connected with the seat and the lens and the reflector assembly and the detector being located in the interior of the light shielding hood, entry of external lighting can be blocked into the interior of the light shielding hood. A signal source, when guided in by the lens, is reflected by the reflector to the detector so as to expand the detection range of the detector.

Compared to the drawbacks of the prior art, the present invention provides a reflector assembly that is coupled to a detector through easy fitting so that through reflection achieved with the reflector, the detector can expand the detection range thereof without being constrained to the limited space available for a small-sized lighting device and also allowing for installation at locations that are not available for installation due to constraint of detection range. Further, a light shielding hood is provided for use in combination with the lens and the housing to effectively block external lighting and thus maintain normal operations of the detector.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 5B is a schematic view illustrating a reflector according to another embodiment of the present invention.

FIG. 9A is an enlarged view of a portion of the fourth embodiment of the present invention.

DETAILED DESCRIPTION OF THE PREFERRED EMBODIMENTS

Figure 1:
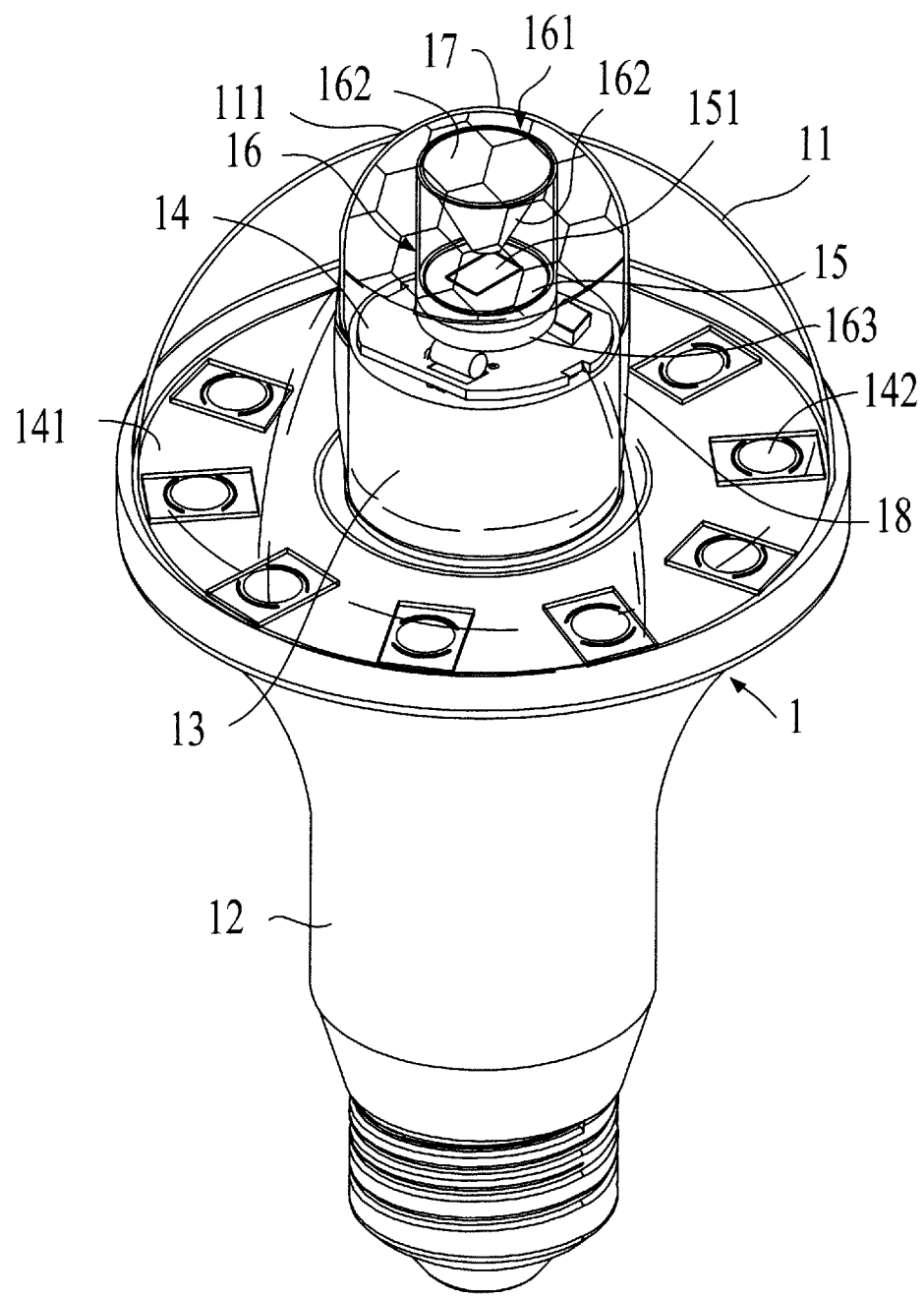
FIG. 1 is a perspective view of the present invention.
Figure 2:
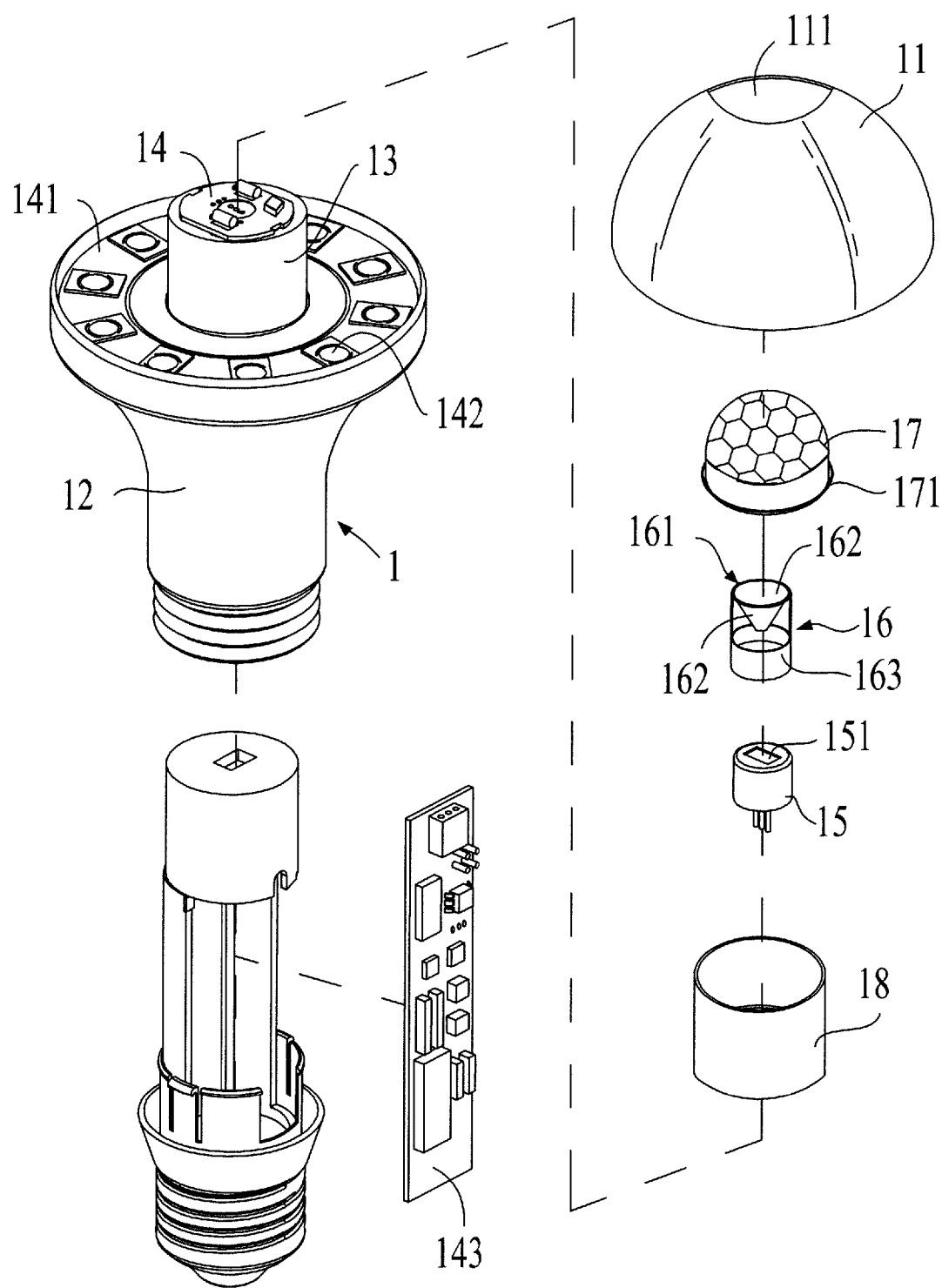
FIG. 2 is an exploded view of the present invention.
Figure 3:
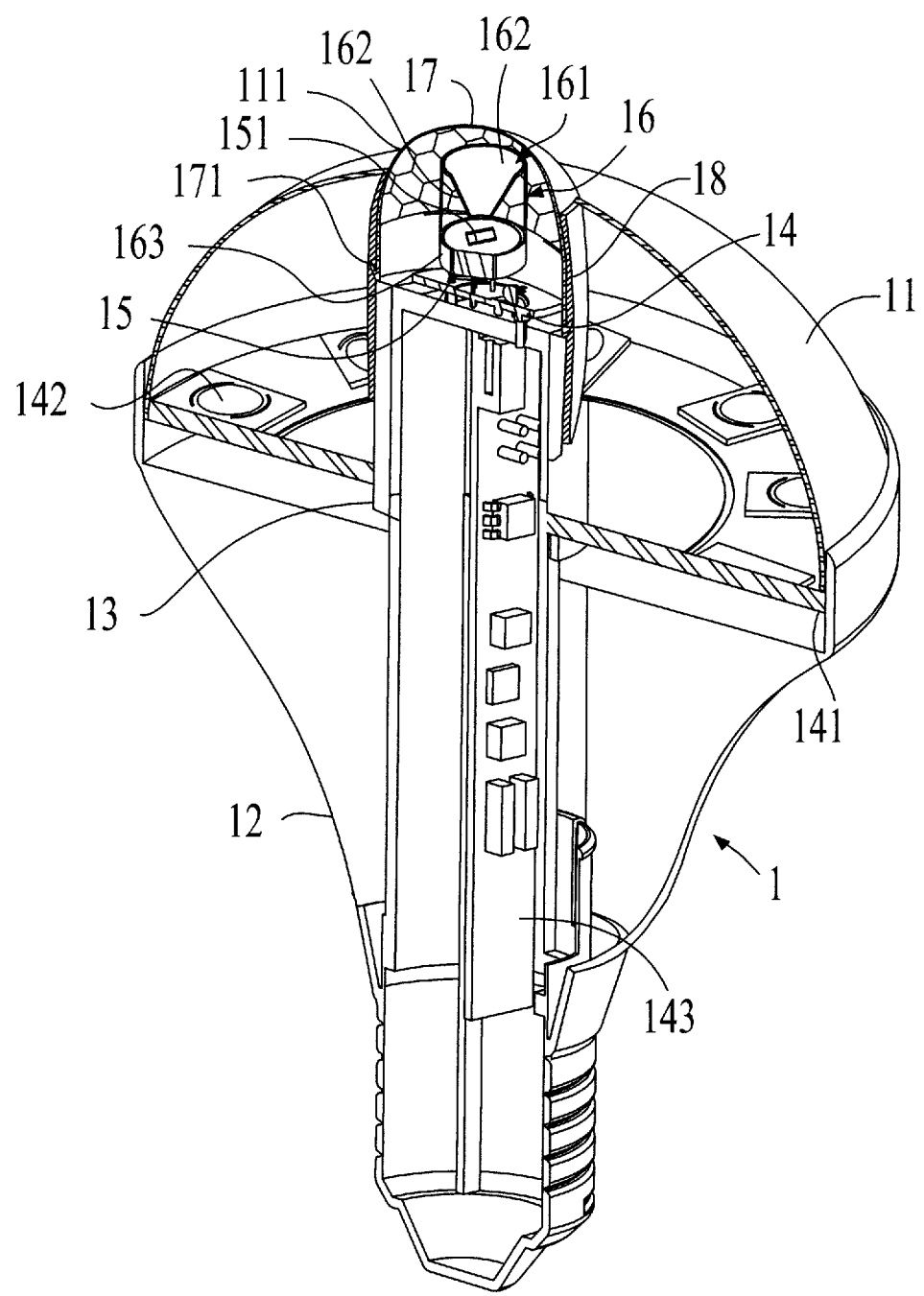
FIG. 3 is a perspective view, in sectioned form, of the present invention.
Figure 4:
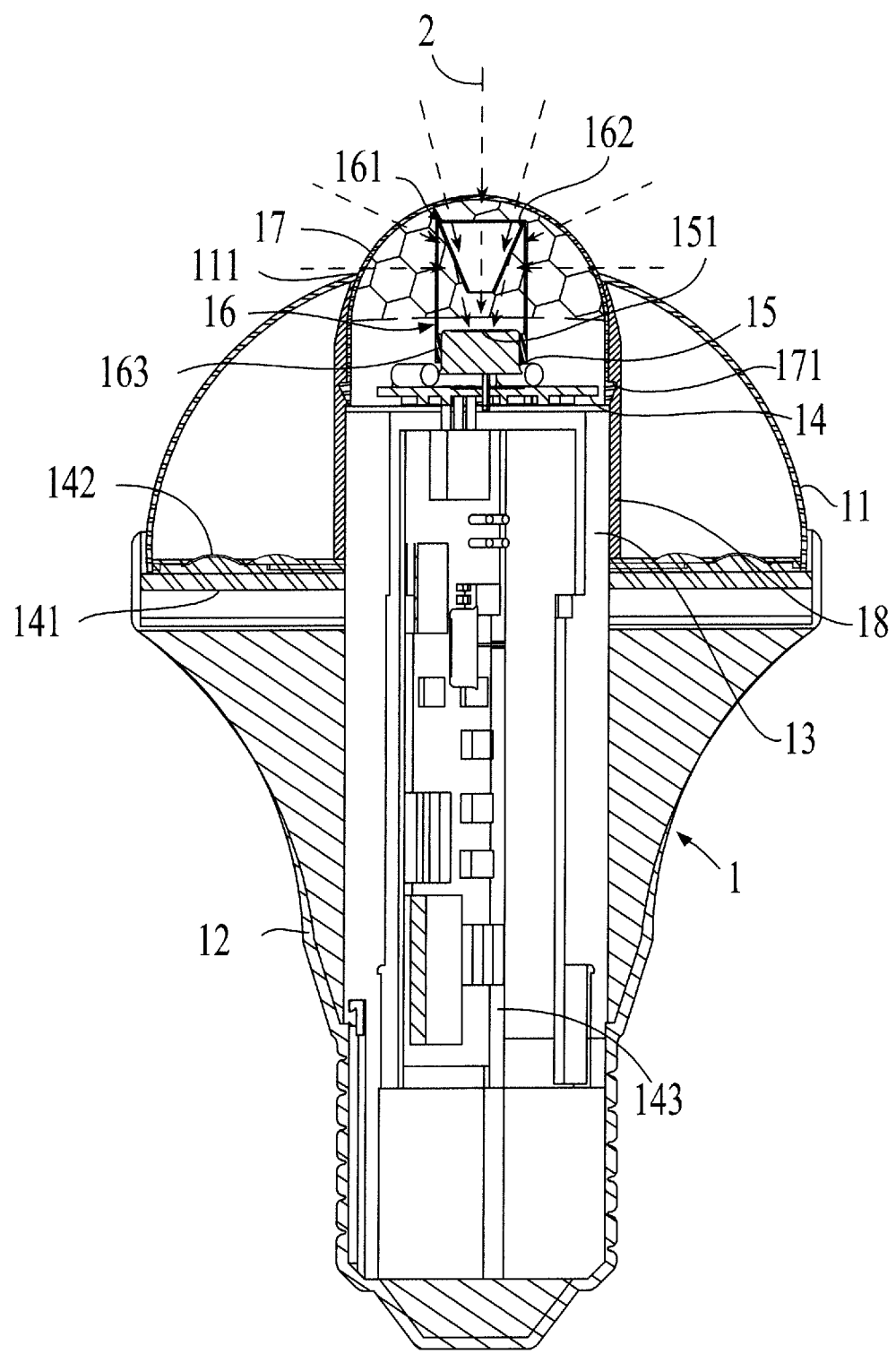
FIG. 4 is a cross-sectional view of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

In general, according to the present invention, an embodiment, which is believed to be the best and most feasible embodiment, with will described in detail with reference to the drawings in order to enhance the understanding of the present invention. Referring to FIGS. 1-4, the present invention provides a lighting device with an expanded detection range. In the following, the term "detection range" used herein includes angle and distance of detection. The lighting device is illustrated as a light bulb that is taken as an example for describing the instant embodiment and comprises: a housing (1) that is composed of an upper casing (11) and a lower casing (12). The upper casing (11) has a top portion in which an opening (111) is formed. The lower casing (12) comprises a power control board (143) arranged in the interior thereof. The lower casing (12) is provided atop with a seat (13). The seat (13) comprises a detector control board (14) mounted thereon to receive a detector (15) to mount thereon. The seat (13) has a circumference along which a light-emitting diode (LED) circuit board (141) is arranged. The LED circuit board (141) comprises at least one or more than one LED (142) mounted thereon. The opening (111) is provided for receiving and fixing a lens (17) that is fit therein. The lens (17) has a distal end that is exposed outside the upper casing (11) of the housing (1). The lens (17) has a lower circumference along which a projecting retainer (171) is formed. A reflector assembly (16) comprises a reflector (161) that condenses a signal source (2) arranged on a top thereof. The reflector (161) has inside and outside surfaces that are subjected to surface treatment, such as electroplating, anodizing, coating, and any other measures that achieve light reflection, so that the inside and outside of the reflector (161) form reflection surfaces (162) for reflecting the signal source (2). The reflector assembly (16) comprises a fixing sleeve (163) arranged on a bottom thereof to fit to and couple to the detector (15). The reflector (161) is in the form of a sandglass and the fixing sleeve (163) is connected and supported at the bottom thereof by means of at least two posts so that the reflection surfaces (162) can directly reflect the signal source (2) at the inside and outside without being shielded. A light shielding hood (18) has a top end extending to the housing (1) or even further upward beyond the housing (1) and connected to the lens (17). A bottom of the light shielding hood (18) is fixed to the seat (13). The light shielding hood (18) is provided to block external light in order to ensure proper operation of the detector (15). The projecting retainer (171) provided on the lower circumference of the lens (17) is engageable with a corresponding slot formed in the light shielding hood (18) to get fixed. The lens (17) can be a Fresnel lens that is commonly used in the art or a lens that achieve the purpose of condensation or focusing the signal source. The signal source (2), when introduced through the lens (17), is reflected by the inside and outside reflection surfaces (162) to get into a detection window (151) arranged in the top of the detector (15) so that the detection range of the present invention an be expanded (where the detection range can be expanded to around 180 degrees in a practical application) thereby overcoming the dead zone issue of the detection range of the conventional device and eliminating the complicated process of adjustment so as to provide an advantage that a user may find the operation easy.

Figure 5:
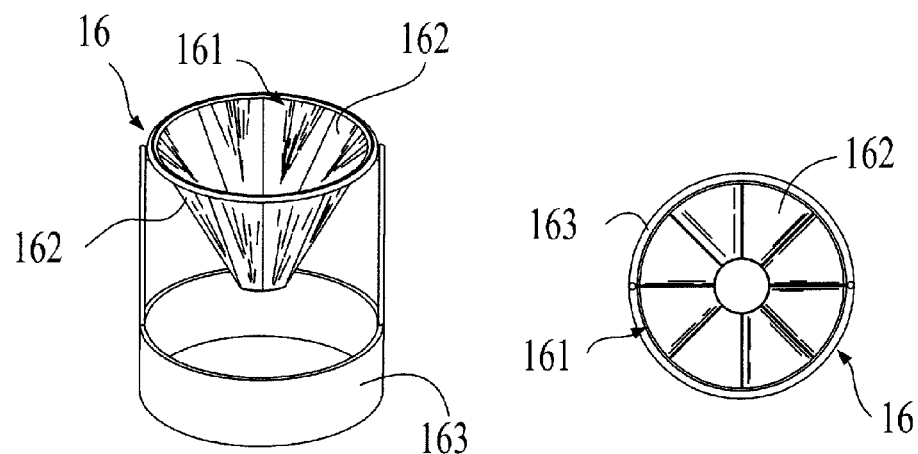
FIG. 5 is a schematic view illustrating a reflector according to another embodiment of the present invention.
Figure 5A:
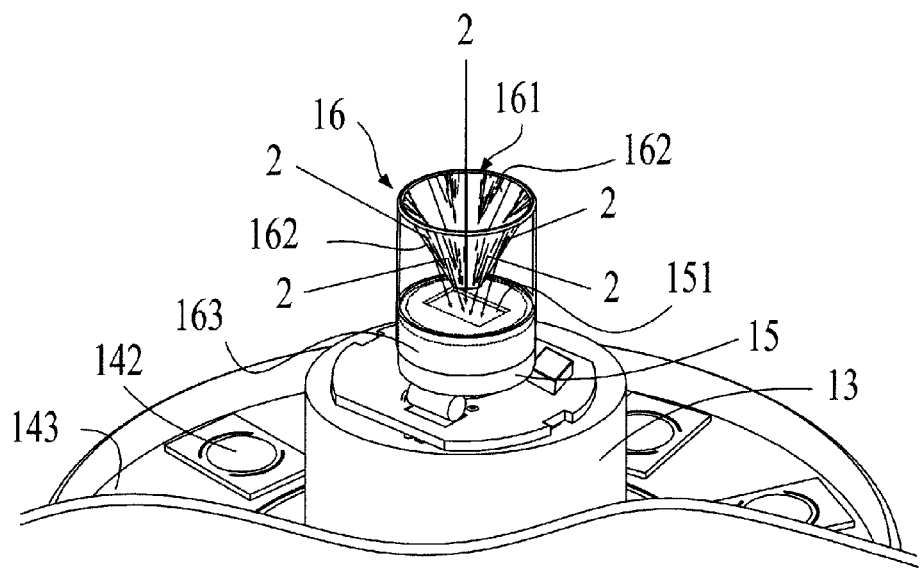
FIG. 5A is a schematic view illustrating a reflector according to another embodiment of the present invention.
Figure 5:
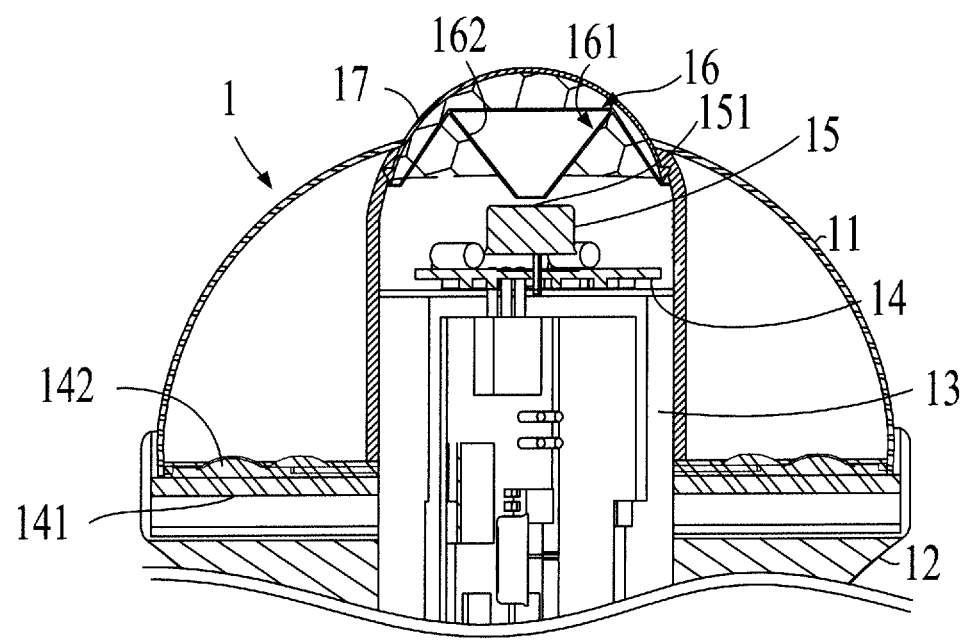

Referring to FIG. 5, the reflection surfaces (162) of the reflector (161) can be of a structural design of rhombus shape. In the drawings, the reflection surface (162) is composed of successive eight-sided rhombus facets; however, four-sided, five-sided, and six-sided rhombuses and the likes may also be used, no limitations being imposed here. As shown in FIG. 5A, the signal source (2) that gets incident at all angles is subjected to reflection by the reflection surface (162) so that the angular range of receiving and reflection is made wider that those of the original sandglass-shaped reflector (161).

Further referring to FIG. 5B, the entirety is of a structure similar to that shown in FIGS. 1-4 and the difference is that the reflector assembly (16) is constructed as being integrally formed with the interior of the light shielding hood (18) or attached thereto through adhesive bonding, so that when the bottom of the light shielding hood (18) is fit to the seat (13), the reflector assembly (16) is located exactly above the detector (15) and there will be no need to provide a fixing sleeve (163) to fit over and hold the detector (15). This arrangement provides various advantages, such as gap-free coupling between components, blocking external lighting, reducing the number of parts, and lowering down cost. Further, the different embodiments of the reflector assembly illustrated in FIGS. 5-5B can be used to replace each other (for example the reflector assembly (16) comprising the multiple rhombus facet reflection surface (162) can be installed in the interior of the light shielding hood (18)), not limited to what described above.

Figure 6:
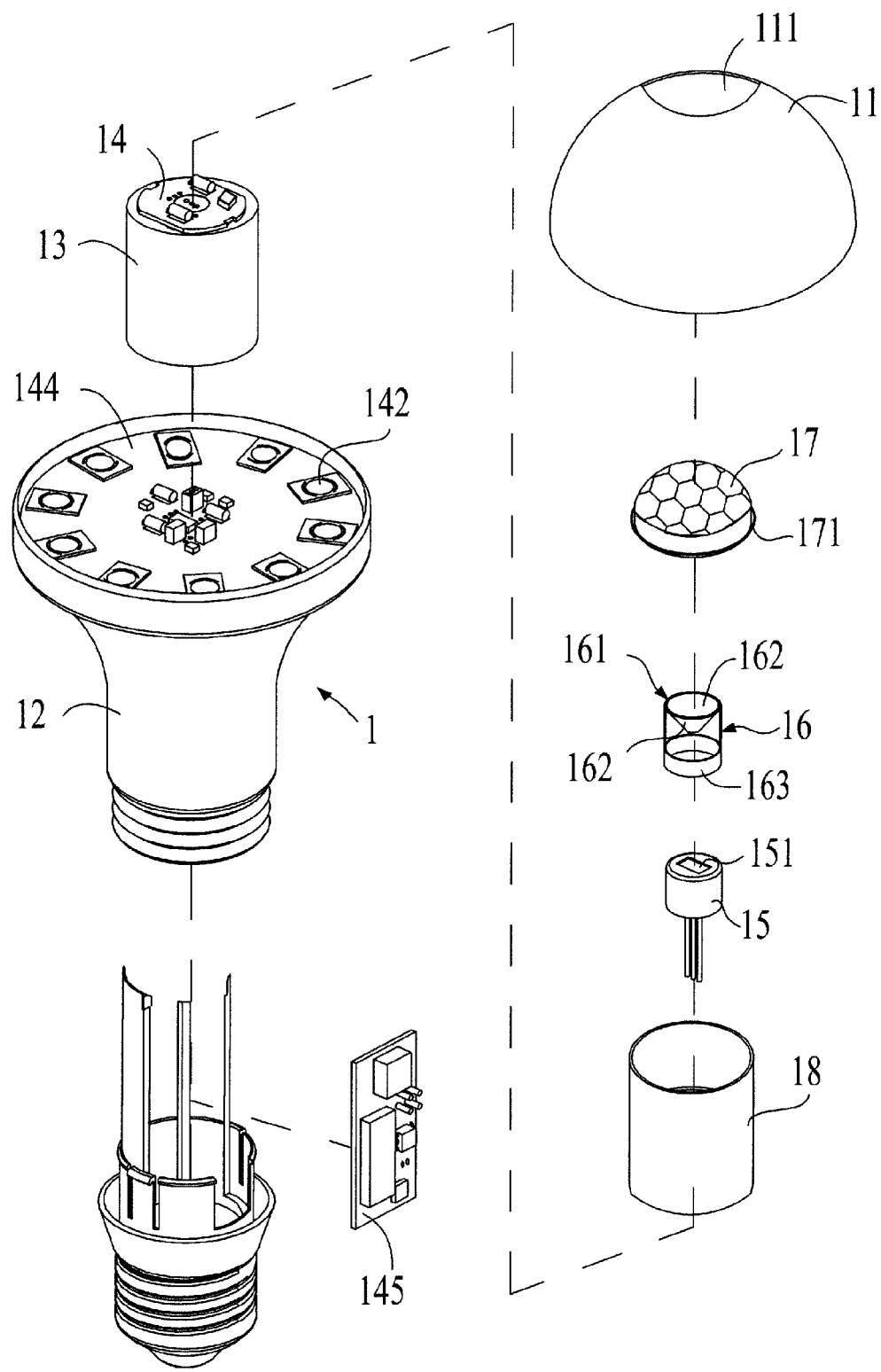
FIG. 6 is an exploded view of a second embodiment of the present invention.
Figure 7:
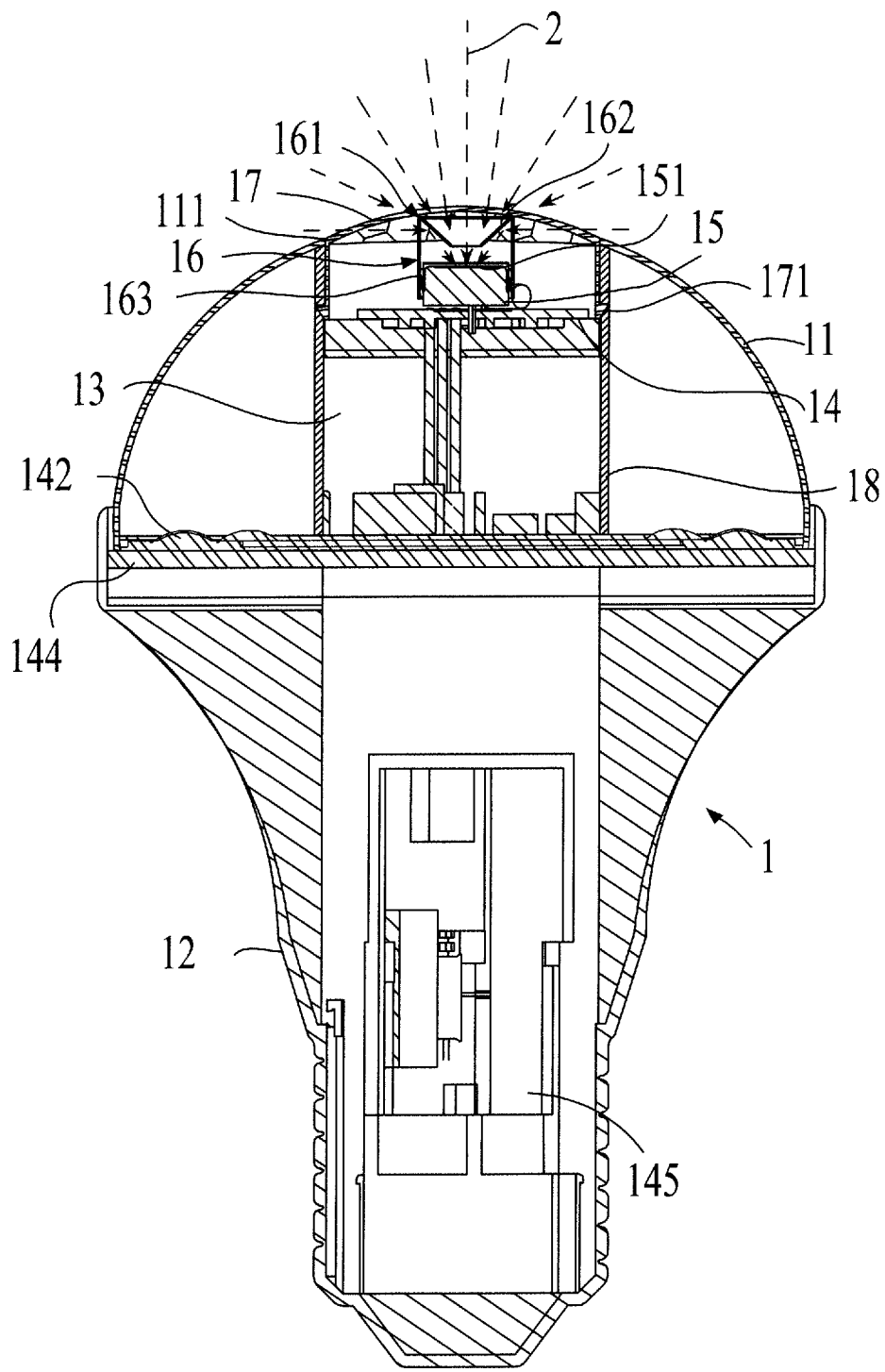
FIG. 7 is a cross-sectional view of the second embodiment of the present invention.
Figure 8:
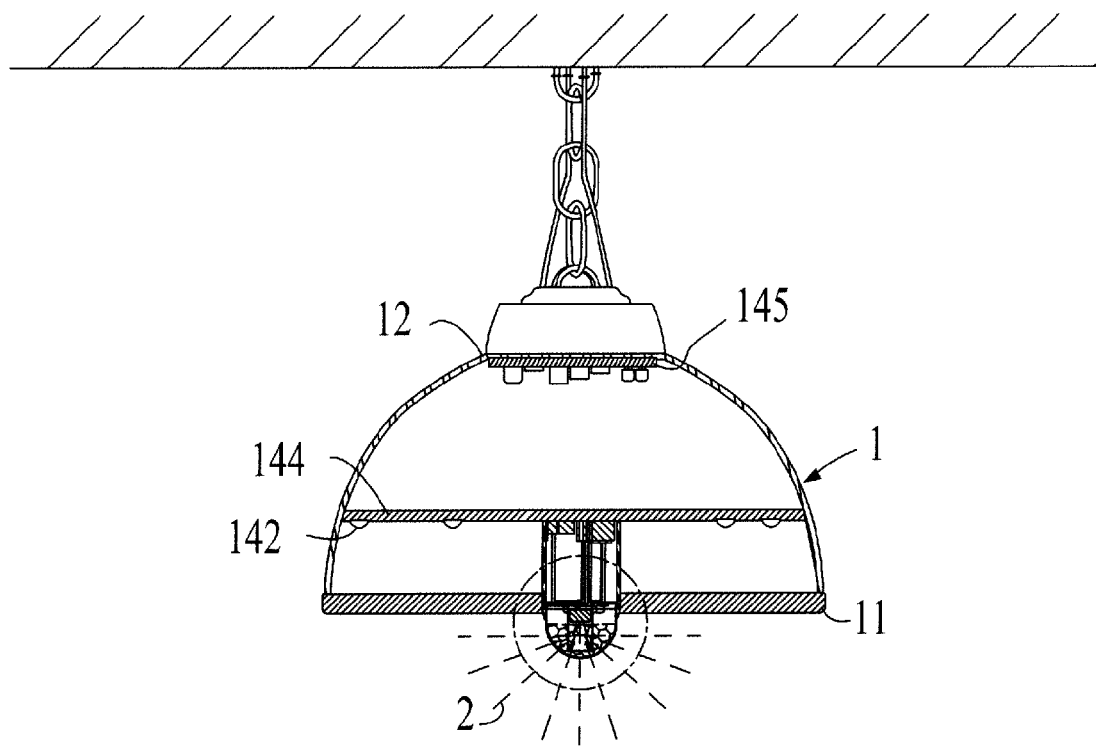
FIG. 8 is a schematic view of a third embodiment of the present invention.
Figure 8A:
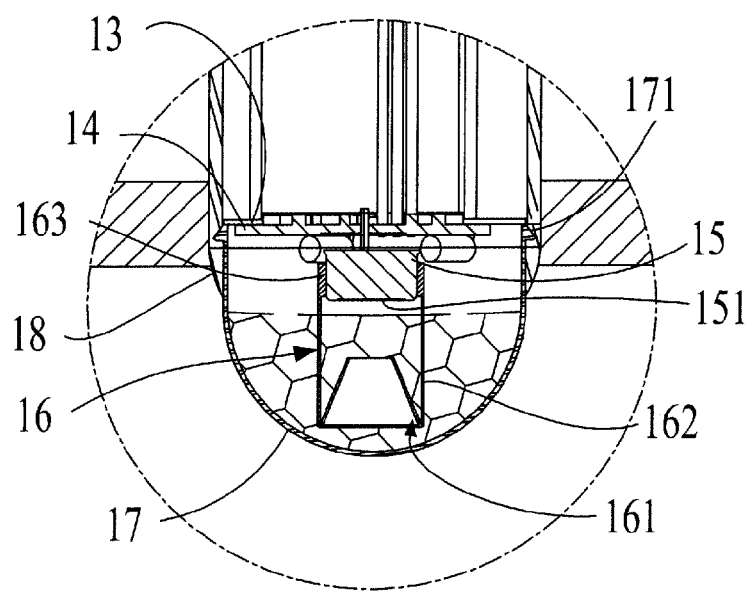
FIG. 8A is an enlarged view of a portion of the third embodiment of the present invention.
Figure 9:
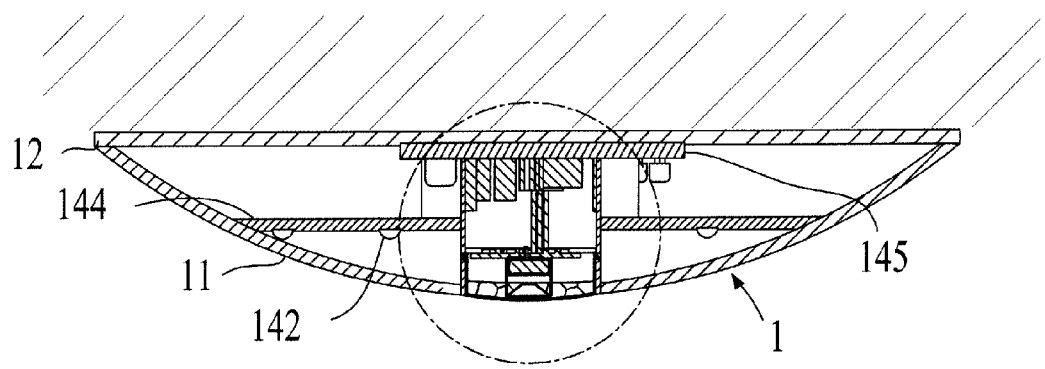
FIG. 9 is a schematic view of a fourth embodiment of the present invention.
Figure 9:
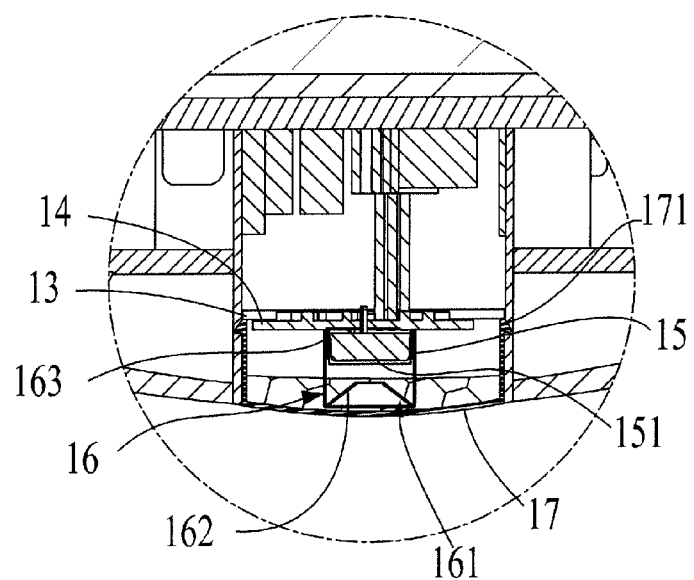
Figure 10:
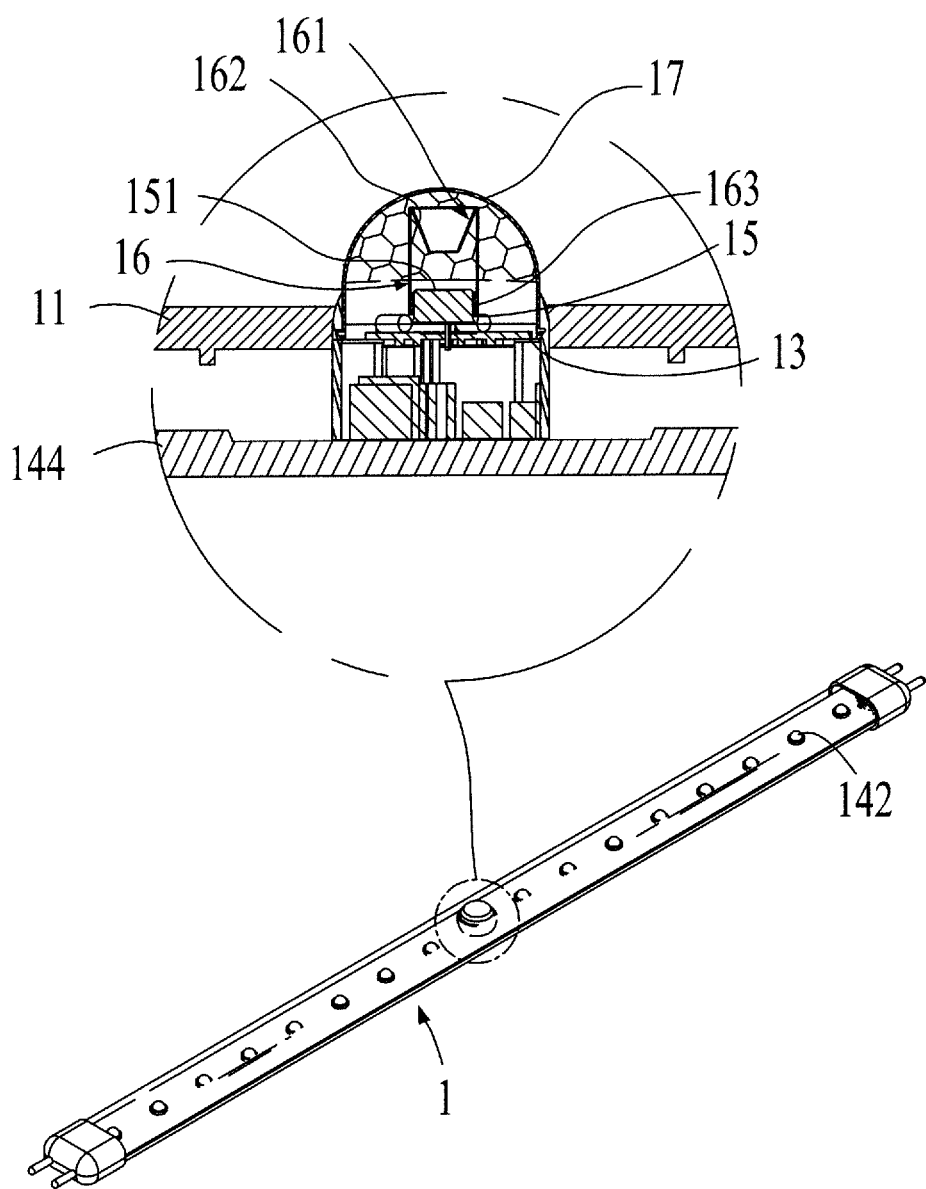
FIG. 10 is a schematic view of a fifth embodiment of the present invention.
Figure 11:
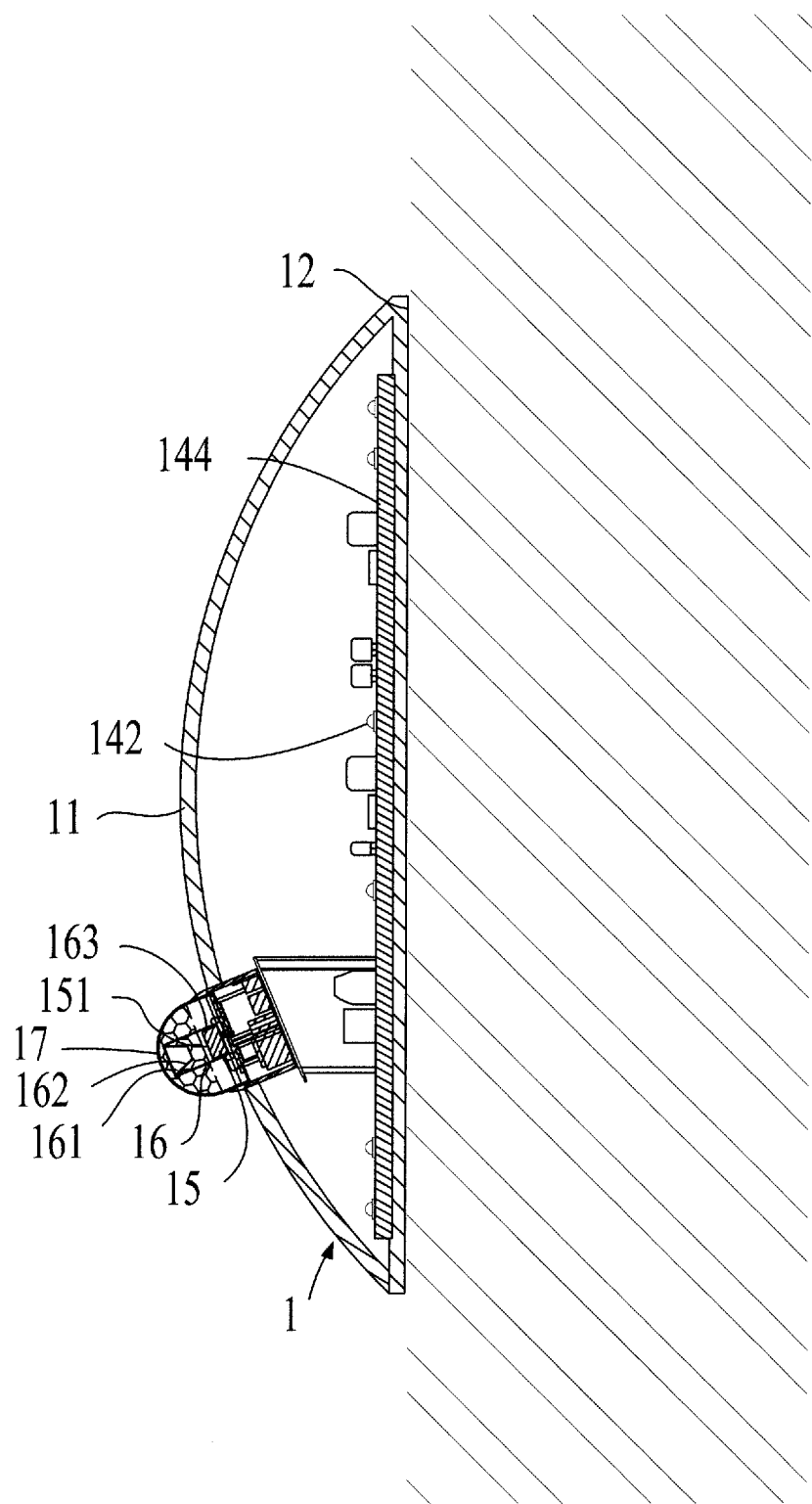
FIG. 11 is a schematic view of a sixth embodiment of the present invention.
Figure 12:
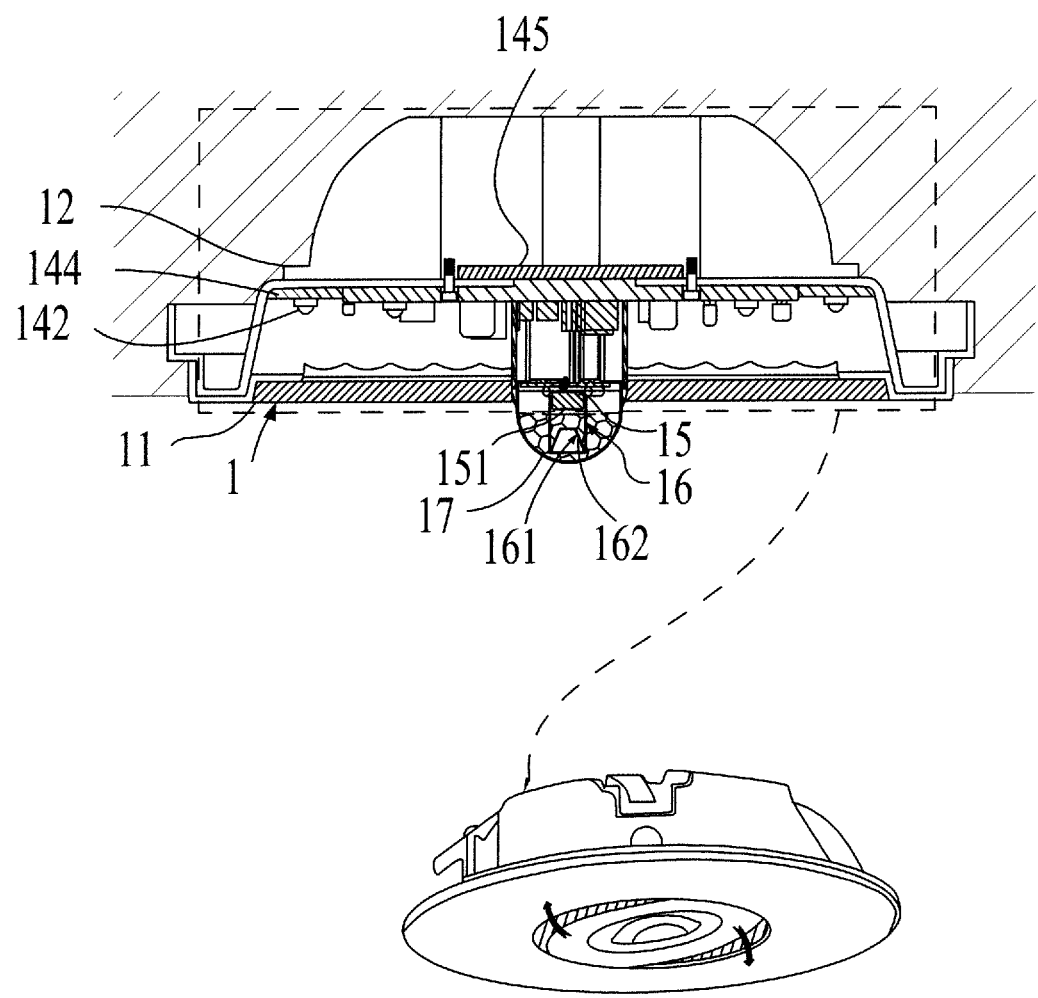
FIG. 12 is a schematic view of a seventh embodiment of the present invention.
Figure 13:
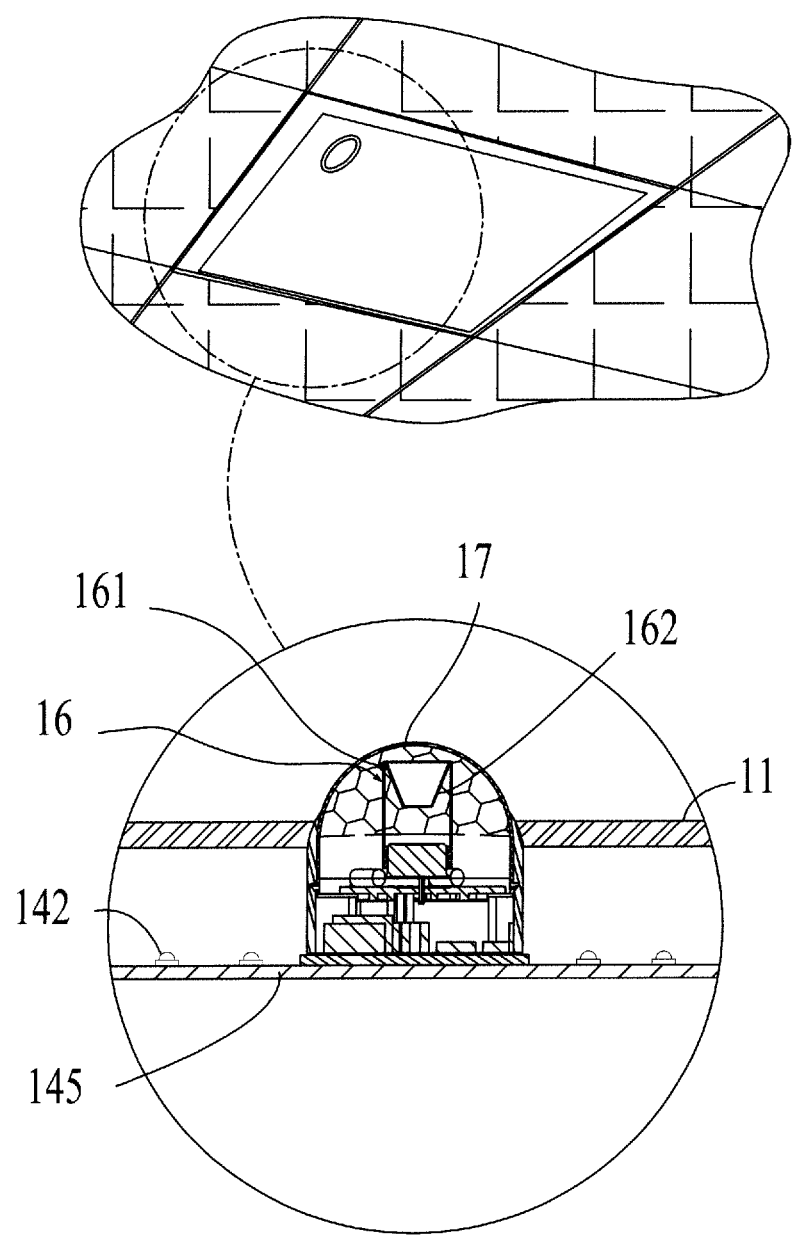
FIG. 13 is a schematic view of an eighth embodiment of the present invention.

Further referring to FIGS. 6-7, a second embodiment of the present invention is shown, in which the light bulb is constructed similar to the embodiment illustrated in FIGS. 1-4, where repeated description of the similar parts will be omitted, and a difference is that the LED circuit board (141) is changed to a primary power board (144) to include power supply components and the LEDs (142) and the power control board (143) that is arranged inside the lower casing (12) is changed to a small-sized power supply board (145) and terminal pins of the detector (15) are lengthened or shortened and the distance between the reflector (161) of the reflector assembly (16) and the fixing sleeve (163) is also changed and the height/length of the light shielding hood (18) is changed, and the curvature of the lens (17) is changed. Such changes of the components are generally provided to suit the needs of a different model of light so that the internal circuit board and certain parts may need to re-design according to the new model and structure of the light. Further referring to FIGS. 8-13, various embodiments respectively associated with pendant light, ceiling light, tubular light, wall-mounted light, and embedded light are illustrated. In all these various models of light, the curvature of the lens (17) is determined to accord to the structural arrangement of the upper casing (11) in order to achieve variation of lead-in angle of the signal source (2). The reflection surface (162) of the reflector assembly (16) may be changed in respect of the inclination thereof so as to change the reflection angle of the signal source (2). The length of the light shielding hood (18) is associated with blocking of the external lighting (such as light from the LED and surrounding light external of the housing) to enter. In addition, the rhombus reflection surface (162) as illustrated in FIGS. 5, 5A, and 5B and the reflector assembly (16) integrally formed with the light shielding hood (18) as well as associated structures can be changed to suit practical needs and usable in various models of light. The present invention is not limited to these embodiments.

In summary, the present invention provides a lighting device with an expanded detection range, which comprises an arrangement of a reflector assembly (16) and a detector (15) inside a housing (1) to allow signal source (2) guided in by a lens (17) to be reflected by inside and outside reflection surfaces (162) into the interior of the detection window (151) and a light shielding hood (18) is provided to couple, with two ends thereof, to the lens (17) and a seat (13) to effectively block light emitting from LEDs (142) and surrounding light external of the housing (1) so as to maintain normal operation of the detector (15). In addition, the arrangement of the reflector assembly (16) is provided to expand an effective detection range.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A lighting device with expanded detection range, comprising:

a housing, which has a hollow interior in which a seat that receives a detector mounted thereto is mounted, the seat having a circumference along which at least one or more than one light-emitting light (LED) is mounted, a lens being fit to an opening formed in a top of the housing corresponding in position to the seat in such a way that a distal end of the lens is exposed outside the housing; a light shielding hood, which has a top end extending to the housing or projecting upward beyond the housing and connected to an end of the lens and a bottom fixed to the seat to block entry of external lighting into interior of the light shielding hood; and a reflector assembly, which comprises a reflector that condenses a signal source arranged on a top thereof, the reflector having inside and outside surfaces that are reflection surfaces, and further comprises a fixing sleeve fixed to a bottom thereof to fit to and couple with the detector, whereby the signal source, when guided in by the lens, is reflected by the reflection surface to the detector so as to expand a detection range.

2. The lighting device with expanded detection range according to claim 1, wherein the reflector is of a sandglass shape.

3. The lighting device with expanded detection range according to claim 1, wherein the reflection surface comprises a plurality of multiple-sided rhombus facets connected together.

4. A lighting device with expanded detection range, comprising:

a housing, which has a hollow interior in which a seat that receives a detector mounted thereto is mounted, the seat having a circumference along which at least one or more than one light-emitting light (LED) is mounted, a lens being fit to an opening formed in a top of the housing corresponding in position to the seat in such a way that a distal end of the lens is exposed outside the housing; a light shielding hood, which has a top end extending to the housing or projecting upward beyond the housing and connected to an end of the lens and a bottom fixed to the seat to block entry of external lighting into interior of the light shielding hood; and a reflector assembly, which is integrally mounted inside the light shielding hood and comprises a reflector that condenses a signal source arranged on a top thereof, the reflector having inside and outside surfaces that are reflection surfaces, and is located exactly above the detector, whereby the signal source, when guided in by the lens, is reflected by the reflection surface to the detector so as to expand a detection range.

\* \* \* \* \*